United States Patent
Fujita et al.

(10) Patent No.: US 10,016,120 B2
(45) Date of Patent: Jul. 10, 2018

(54) CURVATURE SENSOR AND ENDOSCOPE APPARATUS

(71) Applicant: OLYMPUS CORPORATION, Tokyo (JP)

(72) Inventors: Hiromasa Fujita, Hachioji (JP); Ken Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/363,171

(22) Filed: Nov. 29, 2016

(65) Prior Publication Data

US 2017/0071448 A1 Mar. 16, 2017

Related U.S. Application Data

(63) Continuation of application No. PCT/JP2015/064610, filed on May 21, 2015.

(30) Foreign Application Priority Data

May 29, 2014 (JP) .................................. 2014-111697

(51) Int. Cl.
*A61B 1/00* (2006.01)
*A61B 1/005* (2006.01)
(Continued)

(52) U.S. Cl.
CPC ............... *A61B 1/005* (2013.01); *A61B 1/00* (2013.01); *A61B 1/00009* (2013.01);
(Continued)

(58) Field of Classification Search
None
See application file for complete search history.

(56) References Cited

U.S. PATENT DOCUMENTS

| 4,880,970 A * | 11/1989 | Jones ...................... G01L 1/245 250/226 |
| 9,239,429 B2 * | 1/2016 | Sakai ................. A61B 1/00165 |

(Continued)

FOREIGN PATENT DOCUMENTS

| JP | 2008-173397 A | 7/2008 |
| JP | 2011-56280 A | 3/2011 |

(Continued)

OTHER PUBLICATIONS

English translation of International Preliminary Report on Patentability dated Dec. 8, 2016 together with the Written Opinion received in related International Application No. PCT/JP2015/064610.

(Continued)

*Primary Examiner* — Mike Stahl
(74) *Attorney, Agent, or Firm* — Scully, Scott, Murphy & Presser, P.C.

(57) ABSTRACT

A curvature sensor is to be mounted along detection target to allow a curvature of the detection target. The sensor includes a light source, a light guide to guide light from the light source and sensing parts having light absorbability. The sensing parts include absorption bands having different intrinsic absorption patterns and characteristic absorption bands having intrinsic characteristic absorption patterns in the absorption bands. A light detector allows residual light not absorbed by the characteristic absorption bands to be detected, the residual light being included in light of bands corresponding to the characteristic absorption bands and radiated to the sensing parts from the light source. A calculator computes a curvature of the detection target based on a rate of change in the residual light.

10 Claims, 12 Drawing Sheets

(51) Int. Cl.
  *A61B 5/06* (2006.01)
  *G01D 5/353* (2006.01)
  *G01B 11/255* (2006.01)
  *G02B 23/24* (2006.01)
  *G02B 23/26* (2006.01)
  *A61B 1/015* (2006.01)
  *A61B 1/04* (2006.01)
  *A61B 1/06* (2006.01)

(52) U.S. Cl.
  CPC ...... *A61B 1/00045* (2013.01); *A61B 1/00091* (2013.01); *A61B 1/015* (2013.01); *A61B 1/04* (2013.01); *A61B 1/06* (2013.01); *A61B 5/065* (2013.01); *G01B 11/255* (2013.01); *G01D 5/35345* (2013.01); *G02B 23/2476* (2013.01); *G02B 23/26* (2013.01)

(56) References Cited

U.S. PATENT DOCUMENTS

2007/0116415 A1    5/2007   Kobayashi
2011/0098533 A1    4/2011   Onoda et al.
2014/0036261 A1*   2/2014   Fujita ..................... G01B 11/18
                                                                 356/300
2016/0166130 A1*   6/2016   Fujita ..................... G01B 11/24
                                                                 600/118
2017/0035516 A1*   2/2017   Tojo ....................... A61B 1/0017

FOREIGN PATENT DOCUMENTS

JP             4714570 B2     6/2011
WO        2010/050526 A     5/2010
WO    WO 2012/137846 A1   10/2012

OTHER PUBLICATIONS

International Search Report dated Jul. 14, 2015 issued in PCT/JP2015/064610.
Japanese Office Action dated Oct. 10, 2017 in Japanese Patent Application No. 2014-111697.
German Office Action dated Oct. 24, 2017 in German Patent Application No. 112015002537.5.
Chinese Office Action dated Jul. 25, 2017 in Chinese Patent Application No. 201580028417.1.

* cited by examiner

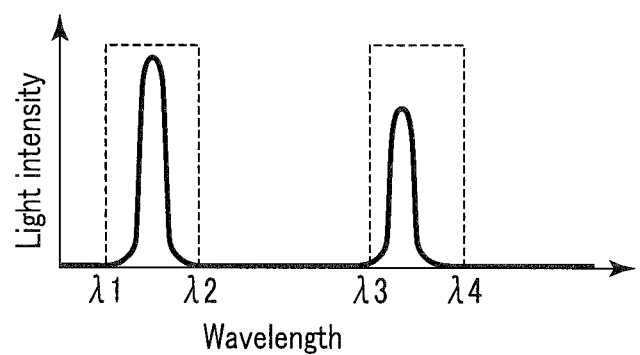
F I G. 21
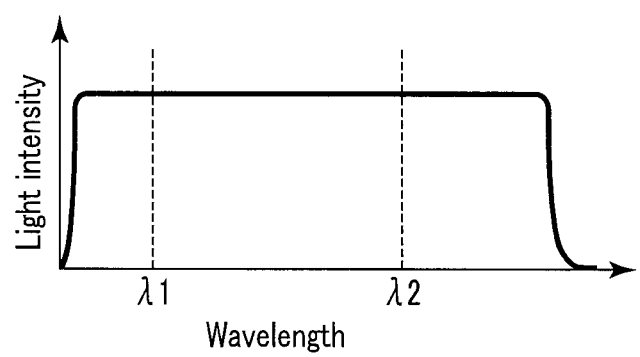
F I G. 22

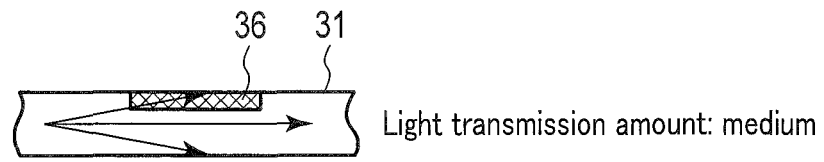
Light transmission amount: medium
F I G. 23
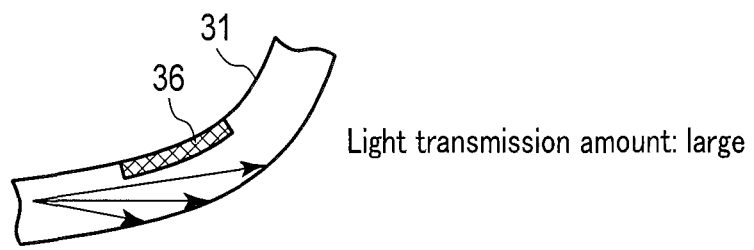
Light transmission amount: large
F I G. 24
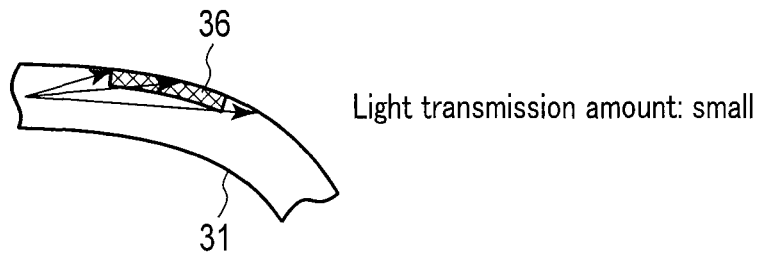
Light transmission amount: small
F I G. 25

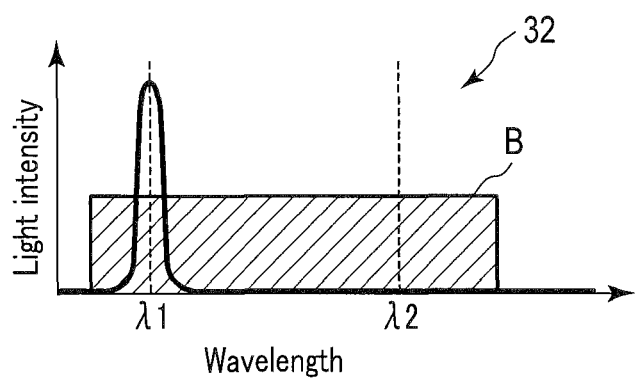
F I G. 27
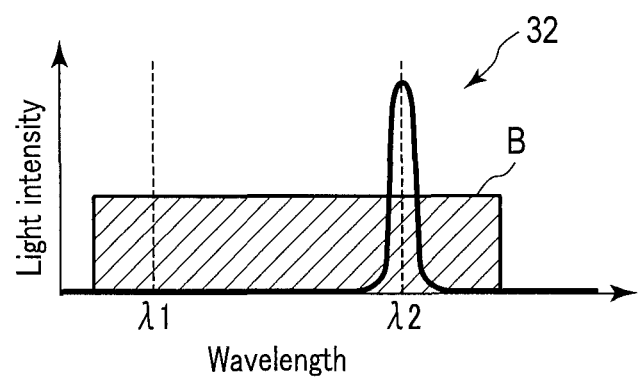
F I G. 28

CURVATURE SENSOR AND ENDOSCOPE APPARATUS

CROSS-REFERENCE TO RELATED APPLICATIONS

This application is a Continuation Application of PCT Application No. PCT/JP2015/064610, filed May 21, 2015 and based upon and claiming the benefit of priority from prior the Japanese Patent Application No. 2014-111697, filed May 29, 2014, the entire contents of all of which are incorporated herein by references.

BACKGROUND OF THE INVENTION

1. Field of the Invention

The present invention relates to a curvature sensor capable of sensing a shape of an endoscope and an endoscope apparatus including the curvature sensor.

2. Description of the Related Art

Conventionally, there has existed an endoscope including a shape detection probe. The shape detection probe can be bent integrally with a scope of the endoscope to sense a shape of the scope. The shape detection probe includes a curvature sensing fiber for transmitting detection light having different wavelength components and a light modulator provided at the curvature sensing fiber to modulate the intensity or wavelength of each of the different wavelength components of the detection light.

The shape detection probe senses a shape of the scope based on the intensity or wavelength of each of the wavelength components before and after the modulation of the light modulator and the distance between the light modulator and the exit end of the curvature sensing fiber. The number of light modulators is equal to that of wavelength components contained in the detection light, and the light modulators selectively absorb one of the different wavelength components (see Japanese Patent No. 4714570, for example).

BRIEF SUMMARY OF THE INVENTION

A curvature sensor according to one embodiment of the present invention is to be provided along a flexible, linear detection target to allow a curvature of the detection target to be sensed, and includes a light source; a light guide provided along the detection target to guide light from the light source; a plurality of sensing parts having light absorbability and provided along a longitudinal direction of the light guide, the sensing parts including absorption bands having different intrinsic absorption patterns and characteristic absorption bands having intrinsic characteristic absorption patterns in the absorption bands; a light detector which allows residual light not absorbed by the characteristic absorption bands to be detected, the residual light being included in light of bands corresponding to the characteristic absorption bands and radiated to the sensing parts from the light source; and a calculator which computes a curvature of the detection target based on a rate of change in the residual light.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 21 is a graph showing another example of the light intensity and wavelength band of the second light source of the curvature sensor shown in FIG. 2.

FIG. 22 is a graph showing another example of the light intensity and wavelength band of the second light source of the curvature sensor shown in FIG. 2.

FIG. 23 is a schematic view showing the principle of sensing a curvature of a detection target using a sensing part in the curvature sensor shown in FIG. 2.

FIG. 24 is a schematic view showing the principle of sensing a curvature of a detection target as in FIG. 23 and showing a state in which the light guide shown in FIG. 23 is curved in a direction of the sensing part.

FIG. 25 is a schematic view showing the principle of sensing a curvature of a detection target as in FIG. 23 and showing a state in which the light guide shown in FIG. 23 is curved in a direction opposite to a direction of the sensing part.

FIG. 27 is a graph showing a wavelength band of light emitted from a second light source of an endoscope apparatus according to a second embodiment and a detection band of a light detector thereof.

FIG. 28 is a graph showing a wavelength band of light emitted from the second light source of the endoscope apparatus according to the second embodiment with time different from the light shown in FIG. 27, and a detection band of the light detector.

DETAILED DESCRIPTION OF THE INVENTION

[First Embodiment]

Figure 1:
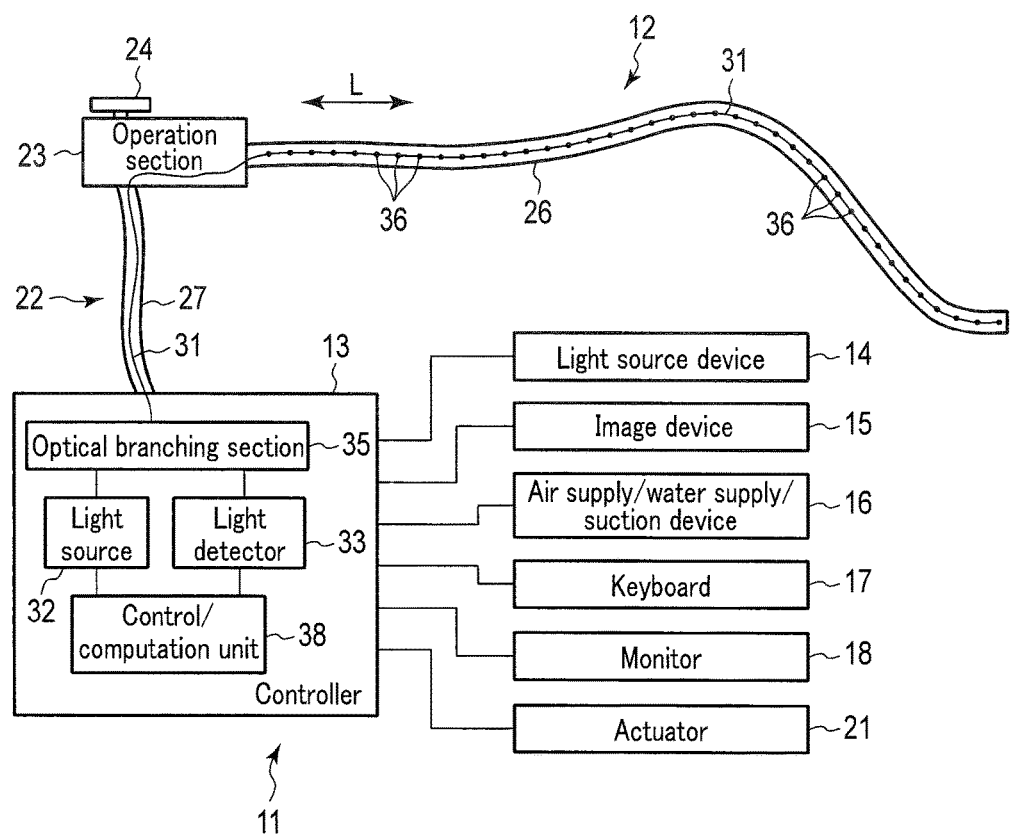
FIG. 1 is a schematic view showing the overall structure of an endoscope apparatus according to a first embodiment.

FIG. 1 is an overall structure diagram of an endoscope apparatus of the present invention. As shown in FIG. 1, an endoscope apparatus 11 includes an endoscope 12, a controller (control device) 13, a light source device (first light source) 14, an image device 15, an air supply/water supply/suction device 16, a keyboard 17, a monitor 18, an actuator 21 and a curvature sensor 22.

The controller 13 controls the light source device 14 to supply light to an illumination lens that is provided at the distal end of the endoscope 12. The controller 13 controls the air supply/water supply/suction device 16 to supply air and water to a nozzle that is provided at the distal end of the endoscope 12 and suck, e.g. liquid and tissue from a living body through the nozzle. The controller 13 controls the image device 15 to process images of a subject imaged through an objective provided at the distal end of the endoscope 12 and then display the processed images on a monitor 18.

The controller 13 is connected to a rotation sensing sensor built in an operation section 23 (described later) of the endoscope 12. The rotation sensing sensor senses a rotation direction and a rotation amount of a knob 24 for operation and sends a sensing signal to the controller 13. The controller 13 actuates an actuator 21 in accordance with the rotation amount sensed by the rotation-sensing sensor to curve an insertion section 26 in a predetermined direction. The actuator 21 is able to give a driving force to curve the insertion section 26 of the endoscope 12 in a predetermined manner. The actuator 21 is configured by a motor such as a servo motor.

As shown in FIG. 1, the endoscope 12 includes a universal cord 27, an operation section 23, and an insertion section 26 extending from the operation section 23 and inserted into a cavity (insertion target). The insertion section 26 is one example of a detection target whose curvature is to be sensed by the curvature sensor 22.

The endoscope 12 is connected to the controller 13, the light source device 14, the image device 15, the air supply/water supply/suction device 16, and the like through the universal cord 27.

Figure 2:
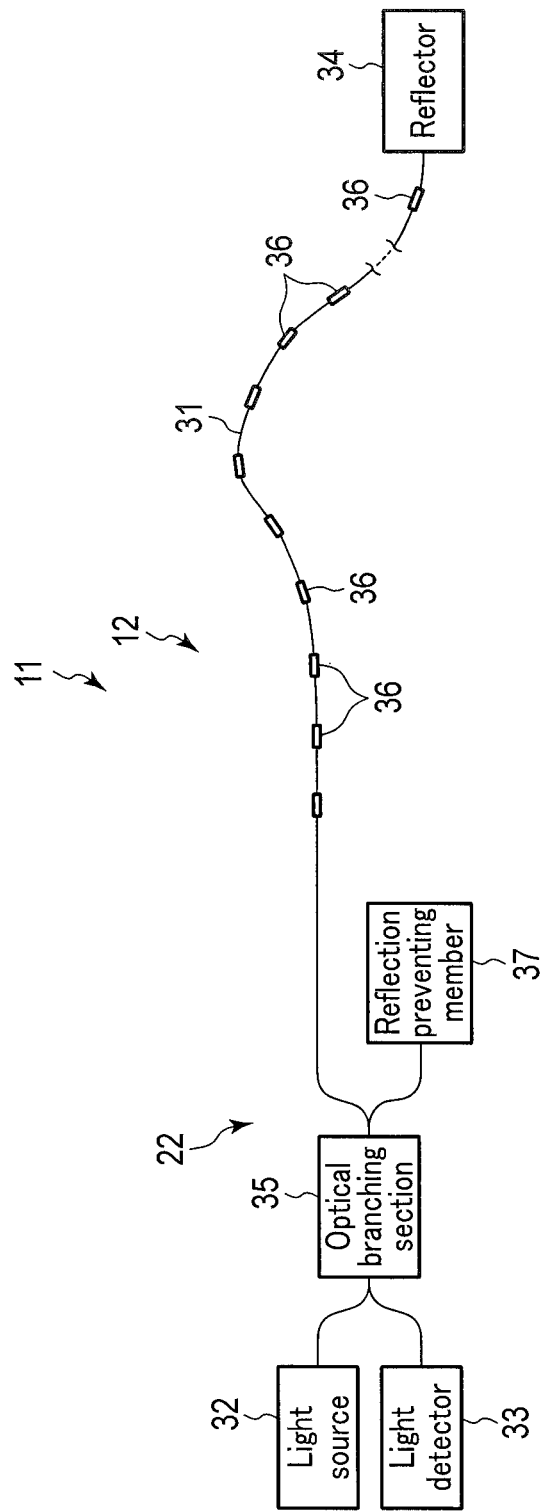
FIG. 2 is a block diagram showing a curvature sensor of the endoscope apparatus shown in FIG. 1.

As shown in FIGS. 1 and 2, the curvature sensor 22 includes a linear light guide 31, a second light source (light source) 32 and a light detector 33 which are provided at one end (the proximal end) of the light guide 31, an optical branching section 35 which supplies light from the second light source to the light guide 31 and which supplies light reflected by a reflector 34 to the light detector 33, a plurality of sensing parts 36 arranged, for example, at fixed intervals halfway in the light guide 31, the reflector 34 provided at the other end (the distal end) of the light guide 31 to reflect light passing through the light guide 31 toward the light detector 33, a reflection preventing member 37 connected to the optical branching section 35, and a control/computation section (calculator) 38 which computes a curvature of the endoscope with light detected by the light detector 33. The second light source 32 is a light source for the curvature sensor 22. The reflection preventing member 37 prevents light, which is branched from the light guide 31 into the light detector 33 and reflected mainly as Fresnel reflection, from narrowing a detection range of the light detector.

The optical branching section 35 is configured by, for example, an optical coupler, a half mirror, or a beam splitter. The reflector 34 is configured by, for example, a mirror formed by evaporating, e.g. aluminum on the end face of an optical fiber.

The light emitted from the second light source 32 is condensed by a condenser lens through the optical branching section 35 and supplied to the light guide 31. Among the light returned from the light guide 31 to the light detector 33, the light emitted from the light guide 31 is received by a light incidence section and collimated into collimation light, and branched, e.g. 90 degrees by the optical branching section 35, and detected by the light detector 33.

Figure 17:
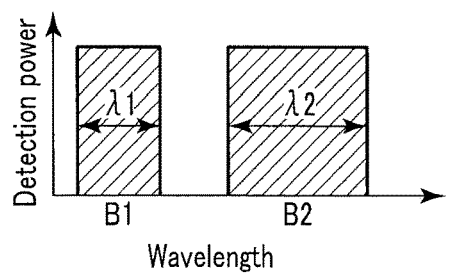
FIG. 17 is a graph showing an example of a detection wavelength band of a light detector of the curvature sensor shown in FIG. 2.
Figure 18:
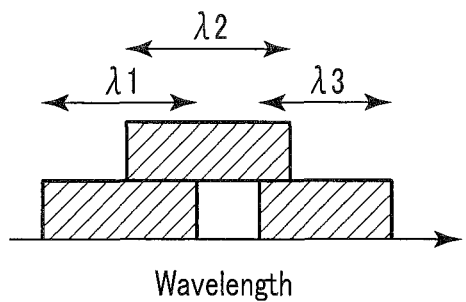
FIG. 18 is a graph showing another example of the detection wavelength band of the light detector of the curvature sensor shown in FIG. 2.

The light detector 33 has a detection wavelength band corresponding to all of the characteristic absorption bands intrinsic to the plurality of sensing parts 36 described later. FIG. 17 shows two detection wavelength bands B1 and B2 corresponding to characteristic absorption bands λ1 and λ2 of, e.g. two sensing parts 36 (actually, the light detector 33 has detection wavelength bands the number of which corresponds to that of characteristic absorption bands of all of the sensing parts 36.) The detection wavelength bands of the light detector 33 can be separated from one another as shown in FIG. 17 or can be overlapped one another to form a single broad detection wavelength band as shown in FIG. 18. As shown in FIG. 17, the detection wavelength bands that are separated from one another can be achieved by, for example, using a spectroscope or placing a color filter or a filter using light interference on a photoelectric conversion element (including on-chip).

Figure 19:
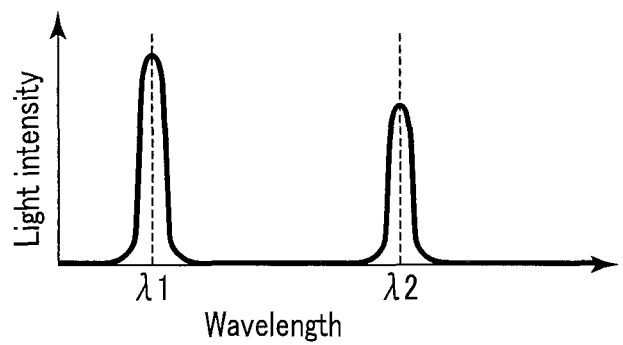
FIG. 19 is a graph showing light intensity and a wavelength band of a second light source of the curvature sensor shown in FIG. 2.

The light of the second light source 32 can be achieved by adding (synthesizing) light of a plurality of relatively small bands, as shown in, e.g. FIG. 19. In this case, the light of each of the small bands corresponds to the characteristic absorption bands (for example, $\lambda 1$ and $\lambda 2$) intrinsic to the sensing parts 36. The wavelength band of one small band is separated from that of light of another small band. The second light source 32 of the present embodiment can be achieved by combining, e.g. a plurality of LEDs or a plurality of LDs (Laser Diodes), which emit small-band light. The second light source 32 can also be configured as described above.

Figure 20:
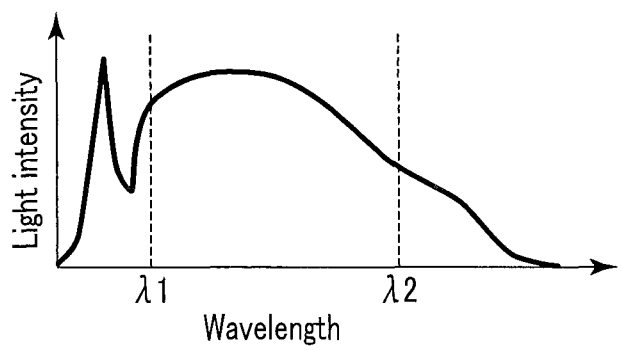
FIG. 20 is a graph showing another example of the light intensity and wavelength band of the second light source of the curvature sensor shown in FIG. 2.

For the second light source 32, as shown in FIG. 20, for example, a light source having a continuous wavelength spectrum, such as white light, can be used. The light (white light) of the second light source 32 shown in FIG. 20 can be generated by exciting, e.g. a fluorescent substance with a short-wavelength light. In this case, the wavelength spectrum of the second light source 32 includes a plurality of characteristic absorption bands (for example, $\lambda 1$ and $\lambda 2$) which correspond to the sensing parts 36.

The light of the second light source 32 can be achieved by adding (synthesizing) light of bands that are much narrower than the small bands shown in FIG. 19, as shown in, for example, FIG. 21. In this case, the wavelength bands of light of the narrower bands include some of the characteristic absorption bands ($\lambda 1$ to $\lambda 2$, $\lambda 3$ to $\lambda 4$) of the sensing parts 36. Even though the second light source 32 is so configured, the light detector 33 is able to sense attenuation of light in a band corresponding to a characteristic absorption band. The second light source 32 shown in FIG. 21 can be achieved by, for example, combining a plurality of LEDs or a plurality of LDs (laser diodes), which emit small-band light.

Furthermore, a light source having substantially a uniform light intensity over a broad wavelength band can be used as the second light source 32, as shown in FIG. 22, for example. It is desirable to use the light source shown in FIG. 22 as the second light source 32 in order to reduce variations in sensing accuracy.

Figure 3:
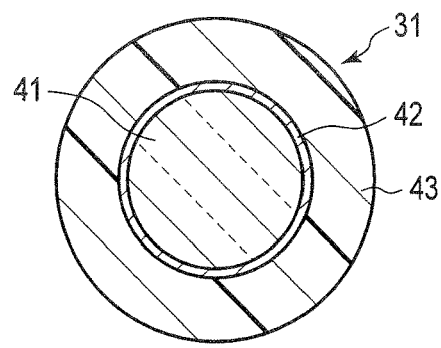
FIG. 3 is a sectional view of a light guide of the curvature sensor shown in FIG. 2, crossing the longitudinal direction of the light guide.

As shown in FIG. 3, the light guide 31 has what is called an optical-fiber-like structure. The light guide 31 includes a core 41 that is formed on translucent materials to transmit light, a cladding 42 that surrounds the core 41 to trap light stably in the core 41, and a jacket 43 that surrounds the cladding 42. The refractive index of the core 41 is higher than that of the cladding 42. The jacket 43 protects the core 41 and the cladding 42 from an external physical and thermal shock.

Figure 4:
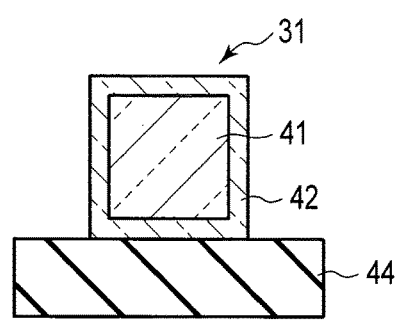
FIG. 4 is a sectional view of another example of the light guide of the curvature sensor shown in FIG. 2, crossing the longitudinal direction of the light guide.

The light guide 31 can be formed like a waveguide on a flexible substrate 44, as shown in FIG. 4. In this case, the light guide 31 includes a core 41 whose cross section is rectangular and a cladding 42 which surrounds the core 41 and whose cross section is rectangular. The functions of the core 41 and cladding 42 shown in FIG. 4 are substantially the same as those of the core 41 and cladding 42 whose cross sections are circular as shown in FIG. 3.

Figure 5:
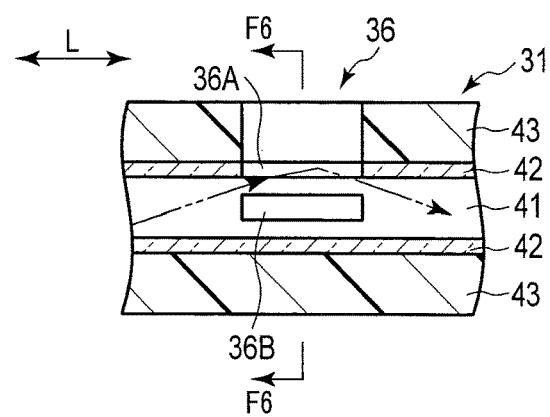
FIG. 5 is a sectional view of the light guide of the curvature sensor shown in FIG. 2, taken along the longitudinal direction of the light guide at a position of a sensing part.

As shown in FIG. 5, each of the sensing parts 36 is provided on the inner side of an opening formed halfway in the cladding 42 of the light guide 31. Each of the sensing parts 36 has light absorbability. Accordingly, the sensing parts 36 perform processes of acquiring light leaked toward the sensing parts 36 through the core 41 (Evanescent light: a few percent of light passing through the core 41), attenuating the light in part of the wavelength bands with absorption spectra intrinsic to the sensing parts 36, and then returning the light to the core 41.

Figure 6:
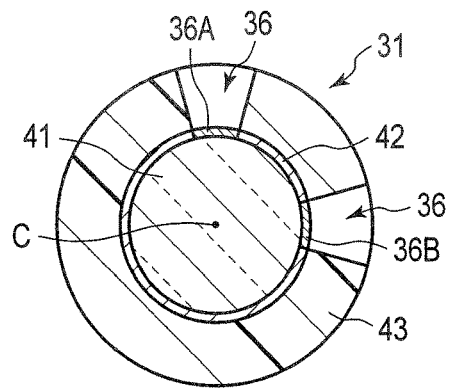
FIG. 6 is a sectional view of the light guide, taken along a line F6-F6 shown in FIG. 5.

As shown in FIGS. 5 and 6, each of the sensing parts 36 includes a first portion 36A and a second portion 36B provided in a position that is rotated, e.g. 90 degrees from the first portion 36A with regard to the central axis C of the core 41 (light guide 31). The first portion 36A and the second portion 36B are provided in the same position with respect to the longitudinal direction L of the insertion section 26 (light guide 31) ; however, they can be displaced with respect to the longitudinal direction L if they fall within a range of the same curvature. The first portion 36A and the second portion 36B are each made of resin materials containing a given amount of coloring matter including pigment etc. (resin materials into which a predetermined concentration of coloring matter is mixed) and have a thickness that is nearly equal to that of the cladding 42. The resin materials containing a given amount of coloring matter can also be formed by causing coloring matter to be contained in a glassy film. The resin materials of the first portion 36A and the second portion 36B have flexibility, which is equal to that of the cladding 42 and a refractive index that is adjusted to be nearly equal to that of the cladding 42. The first portion 36A and the second portion 36B are embedded into the opening of the cladding 42. If, therefore, the sensing parts 36 are formed from the first portion 36A and the second portion 36B which are displaced 90 degrees with regard to the central axis C, it is possible to sense not only a curvature of a detection target but also a direction in which the detection target is curved. They need not be displaced about 90 degrees in strictly the same position in the longitudinal direction, and it does not matter that they are displaced in the longitudinal direction within a range of the same curvature. Here, the refractive index of the sensing parts 36 (first portion 36A and second portion 36B) is not limited to a value that is smaller than that of the core 41 (in this case, the light in the core 41 leaks out to the sensing parts 36 as an Evanescent wave). The refractive index of the sensing parts 36 can be set equal to or higher than that of the core 41 and, in this case, light leaks out to the sensing parts 36 from the core 41 and attenuates in the sensing parts 36. In the present embodiment, the sensing parts 36 are formed by the first portion 36A and the second portion 36B, which are displaced 90 degrees with regard to the central axis C; however, the sensing parts 36 can be formed by the first portion 36A only.

Figure 7:
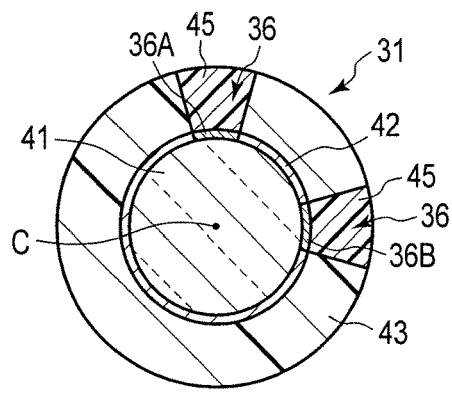
FIG. 7 is a sectional view showing a light guide of another example of the curvature sensor shown in FIG. 2, crossing the longitudinal direction of the light guide at a position of a sensing part.
Figure 8:
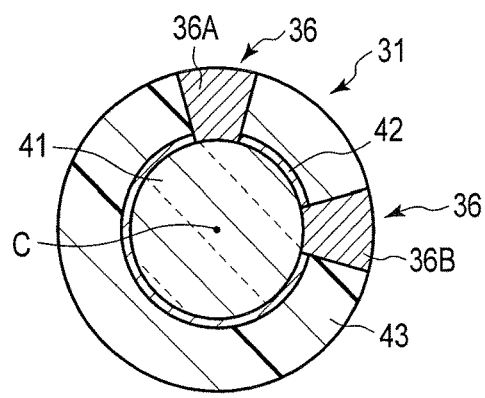
FIG. 8 is a sectional view showing a light guide of another example of the curvature sensor shown in FIG. 2, crossing the longitudinal direction of the light guide at a position of a sensing part.

The first portion 36A or the second portion 36B of the sensing parts 36 is not limited to the above. As shown in FIG. 7, the curvature sensor 22 may have protectors 45 on (outside) the first portion 36A and the second portion 36B to protect these portions. The protectors 45 are formed of the same material as that of, e.g. the jacket 43. In the case of FIG. 7, the refractive index of the protectors 45 is lower than that of the sensing parts 36 and thus the residual light absorbed by the characteristic absorption bands in the sensing parts 36 does not leak to the protectors 45 outside the sensing parts 36 but returned to the core 41. Furthermore, as shown in FIG. 8, the first portion 36A and the second portion 36B can be formed to have a thickness that is nearly equal to the sum of the thickness of the cladding 42 and that of the jacket 43. In the case of FIG. 8, the refractive index of the sensing parts 36 is set lower than that of the core 41. In FIG. 8, light mainly including Evanescent wave, which leaks out to the sensing parts 36 from the core 41, can be absorbed by absorption bands 46 (characteristic absorption bands) of the sensing parts 36, and the residual light that is not absorbed by the absorption bands 46 can be returned to the core 41 again.

As shown in FIGS. 9 to 12, each of the sensing parts 36 (first portion 36A and second portion 36B) has an absorption band 46 having its intrinsic absorption pattern. The absorption band 46 includes a plurality of characteristic absorption bands $\lambda(\lambda 1$ to $\lambda n)$ (FIGS. 9 to 12 show only one of the characteristic absorption bands $\lambda$). One of the characteristic absorption bands in the absorption band 46 differs in wavelength band from the other characteristic absorption bands in the absorption band 46. One of the sensing parts 36 (first portion 36A and second portion 36B) has an absorption band 46 different from that of the other sensing part 36. The absorption bands 46 of the sensing parts 36 and their characteristic absorption bands shown in FIGS. 9 to 12 are one example, and the other different absorption spectrum patterns can be adopted. Moreover, the number of characteristic absorption bands included in a first absorption band 46A coincides with, for example, the total number of sensing parts 36 provided halfway in the light guide 31. More specifically, when the total number of sensing parts 36 provided halfway in the light guide 31 is 10, the number of characteristic absorption bands included in the first absorption band 46A is set to, e.g. 10 and when the total number of sensing parts 36 is 20, the number of characteristic absorption bands included in the first absorption band 46A is set to, e.g. 20. The number of characteristic absorption bands can be set equal to or larger than the total number of sensing parts 36. Thus, the sensing accuracy of the curvature and the direction of curve can be improved further.

Figure 9:
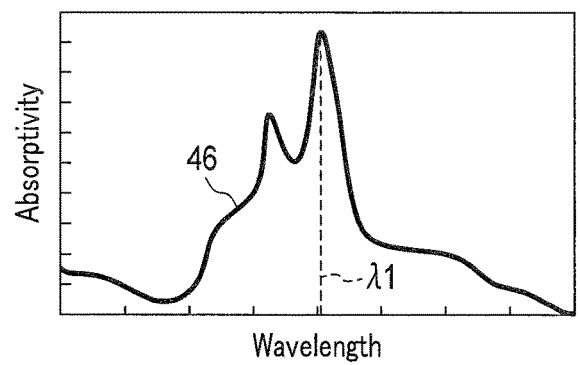
FIG. 9 is a graph showing an absorption band and a characteristic absorption band ($\lambda 1$) of a sensing part of the curvature sensor shown in FIG. 2.
Figure 10:
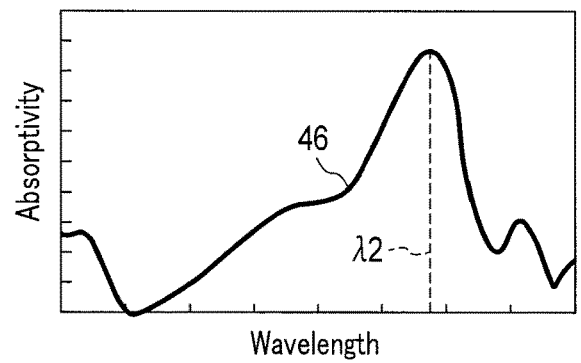
FIG. 10 is a graph showing an absorption band and a characteristic absorption band ($\lambda 2$) of a sensing part of the curvature sensor shown in FIG. 2.
Figure 11:
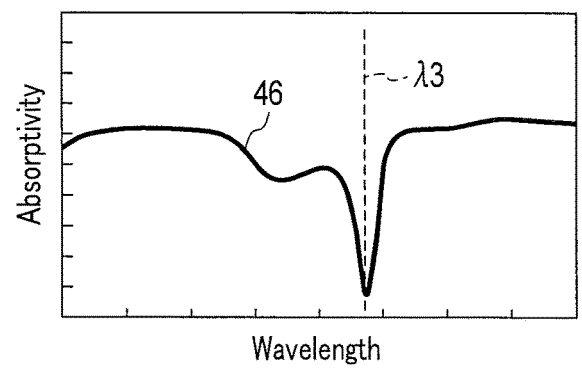
FIG. 11 is a graph showing an absorption band and a characteristic absorption band ($\lambda 3$) of a sensing part of the curvature sensor shown in FIG. 2.
Figure 12:
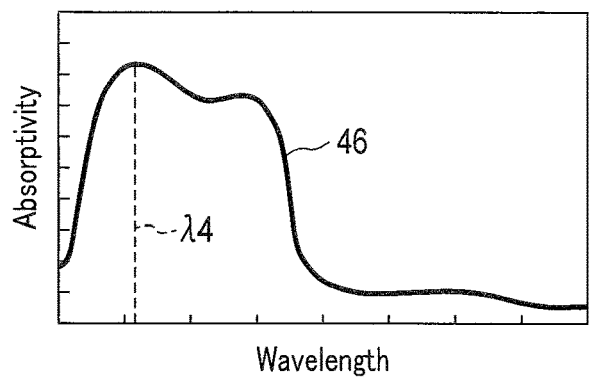
FIG. 12 is a graph showing an absorption band and a characteristic absorption band ($\lambda 4$) of a sensing part of the curvature sensor shown in FIG. 2.

The characteristic absorption bands may have, e.g. a crest portion (peak portion) in the spectrum pattern as shown in FIGS. 9, 10 and 12 and may have, e.g., a trough portion in the spectrum pattern as shown in FIG. 11. The first portion 36A and the second portion 36B included in one sensing part 36 vary in the composition of resin and coloring matter and in the amount of coloring matter contained in resin so as to have different absorption bands 46.

In the present embodiment, the band of the absorption band 46 of one sensing part 36 overlaps part or all of the band of the absorption band 46 of another sensing part 36. Furthermore, the band of the characteristic absorption band of one sensing part 36 overlaps that of the characteristic absorption band of another sensing part 36. In the present embodiment, there is a difference in light absorptivity between the characteristic absorbing bands; thus, it is possible to find a point of the sensing part 36 at which the detection target is curved.

The coloring matter contained in the sensing parts 36 varies in the wavelength of light that can be absorbed according to the color of the outward appearance. Thus, the absorption bands 46 (absorption patterns) and characteristic absorption bands (characteristic absorption patterns) of the sensing parts 36 can freely be designed by adjusting the types and amounts (concentrations) of coloring matter contained in the sensing parts 36 and if a plurality of coloring matters are mixed, adjusting, e.g. the compounding ratio of the coloring matters.

Figure 13:
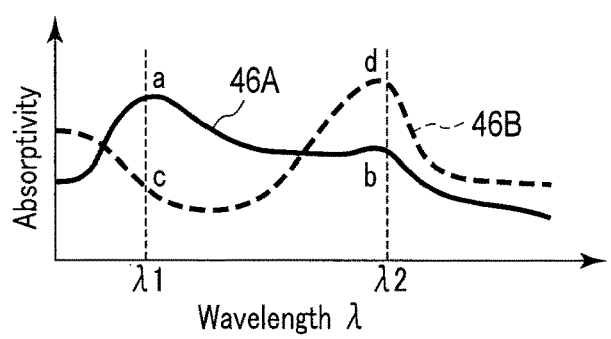
FIG. 13 is a graph showing a first absorption band and a first characteristic absorption band ($\lambda 1$) of a first sensing part of the curvature sensor shown in FIG. 2 and a second absorption band and a second characteristic absorption band ($\lambda 2$) of a second sensing part thereof.
Figure 26:
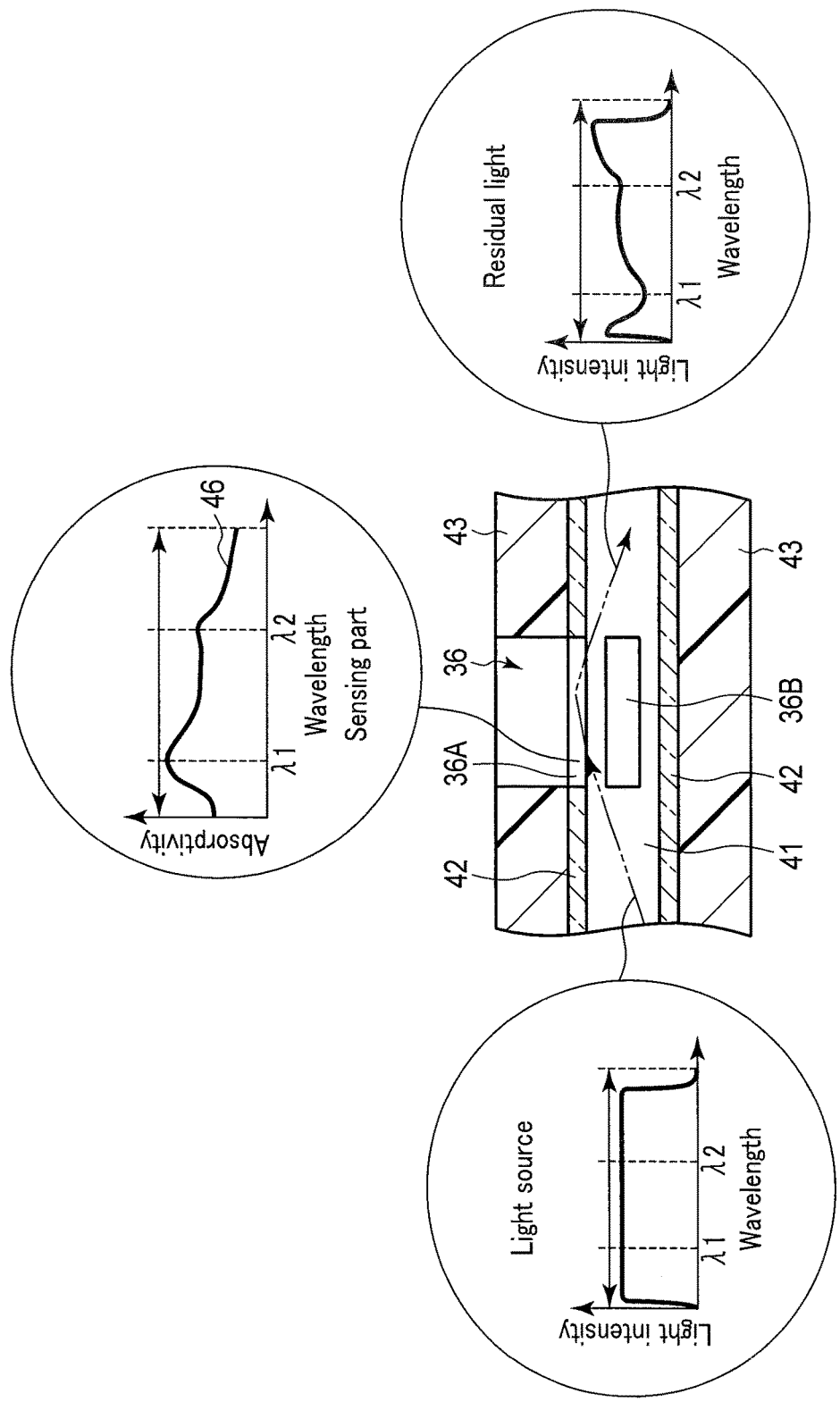
FIG. 26 is a schematic view showing a process of attenuating light emitted from the second light source and passing through the core and returning the light to the core again in the curvature sensor shown in FIG. 2.

Next, a method of sensing a curvature of a detection target using the curvature sensor 22 of the present embodiment will be described with reference to FIGS. 13 and 26. Here, in terms of descriptions, the total number of sensing parts 36 is defined as two; however, actually, there are two or more sensing parts 36. FIG. 13 shows a typical example of absorption spectrum patterns of two sensing parts 36. The two sensing parts 36 have different absorption bands 46 and different characteristic absorption bands. More specifically, the first sensing part 36 has a first absorption band 46A and two characteristic absorption bands included in the first absorption band 46A. The second sensing part 36 has a second absorption band 46B and two characteristic absorption bands included in the second absorption band 46B.

When light falls on the first sensing part 36 from the second light source 32, the light attenuates in the first sensing part 36 with the absorptivity of the first absorption band 46A indicated by the solid line in FIG. 13. At this time, in the first characteristic absorption band $\lambda 1$, the light attenuates with absorptivity (rate) a. In the second characteristic absorption band $\lambda 2$, the light attenuates with absorptivity (rate) b. In other words, as shown in FIG. 26, the residual of light (residual light) absorbed by an absorption pattern (absorption band) intrinsic to the first sensing part 36 is returned to the core 41 of the light guide 31, reflected by the reflector 34 and detected by the light detector 33.

Similarly, when light falls on the second sensing part 36 from the second light source 32, the light attenuates in the second sensing part 36 with the absorptivity of the second absorption band 46B indicated by the broken line in FIG. 13. At this time, in the first characteristic absorption band $\lambda 1$, the light attenuates with absorptivity (rate) c. In the second characteristic absorption band $\lambda 2$, the light attenuates with absorptivity (rate) d.

As described above, in the present embodiment, the light absorptivity in the characteristic absorption bands ($\lambda 1$ to $\lambda n$) varies among the sensing parts 36. If, therefore, the light detector 33 detects light (residual light) which is not absorbed by a sensing part 36 but falls within a band corresponding to the characteristic absorption band and then the control/computation section 38 computes a curvature from the light intensity (light amount) of the residual light, it is possible to sense which of the sensing parts 36 is curved and how it is curved. It is desirable that the ratio of variations in intensity (light amount) of light (residual light) reaching the light detector 33 to variations of a curvature of a detection target (insertion section 26) be constant. When the ratio of variations in intensity (light amount) of light (residual light) reaching the light detector 33 to variations of a curvature of a detection target (insertion section 26), the curvature of a detection target (insertion section 26) can be computed on the basis of experimental values of intensity (light amount) of light (residual light) relative to a curvature of a detection target (insertion section 26).

For example, as shown in FIG. 23, the insertion section 26 being detection target is disposed straightly, and part of light transmitted through the light guide 31 is attenuated by the sensing part 36 and thus becomes residual light. The light transmission amount of the residual light and that of light not passing through the sensing part 36 are both medium amounts. When the insertion section 26 is curved in a direction of the sensing part 36 as shown in FIG. 24, the amount of light attenuated by the sensing part 36 is decreased. Therefore, a relative light transmission amount of light not passing through the sensing part 36 in the state of FIG. 24 becomes larger than that in the state of FIG. 23 (on the other hand, the light amount of residual light attenuated by the sensing part 36 becomes small).

When the insertion section 26 is curved in a direction opposite to a direction of the sensing part 36 as shown in FIG. 25, the amount of residual light attenuated by the sensing part 36 is increased. Therefore, a relative light transmission amount of light not passing through the sensing part 36 in the state of FIG. 25 becomes smaller than that in the state of FIG. 23 (a relative light transmission amount of residual light becomes large). Since the light amount of residual light varies with directions in which the detection target and the light guide 31 are curved, the curvature and curve direction at a point where a sensing part 36 is provided can be sensed with high accuracy on the basis of the rate of the variations.

The sensing part 36 includes a first portion 36A and a second portion 36B, which are displaced 90 degrees with regard to the central axis C as described above. Thus, the curvature sensor 22 is able to sense not only a curve within one plane (e.g. a curve in the Up and Down (UD) direction) but also a curve within a plane intersecting (orthogonal to) the one plane (e.g. a curve in the Right and Left (RL) direction). In the foregoing descriptions, the sensing part 36 exerts an optical influence (attenuation of light intensity) upon light passing through the light guide 31 toward the reflector 34 from the second light source 32. However, the sensing parts 36 of the present embodiment are also able to exert an optical influence (attenuation of light intensity) upon light passing through the light guide 31 toward the light detector 33 from the reflector 34.

Figure 14:
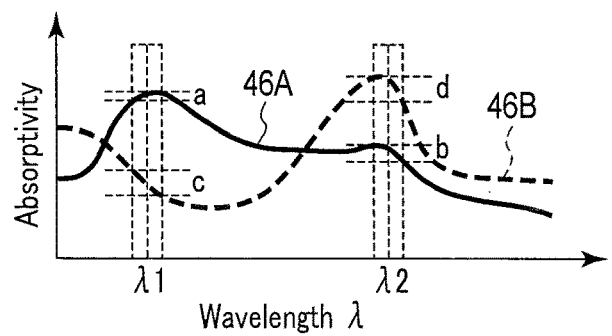
FIG. 14 is a graph showing another example of the first absorption band and first characteristic absorption band ($\lambda 1$) of the first sensing part of the curvature sensor shown in FIG. 2 and the second absorption band and second characteristic absorption band ($\lambda 2$) of the second sensing part thereof.

As shown in FIG. 14, the characteristic absorption bands (λ1, λ2) in the sensing part 36 can be defined as ones over a fixed wavelength band. As the absorptivity in each of the characteristic absorption bands, for example, an intermediate value between the maximum and minimum values of the absorptivity included in the characteristic absorption band can be adopted.

Figure 15:
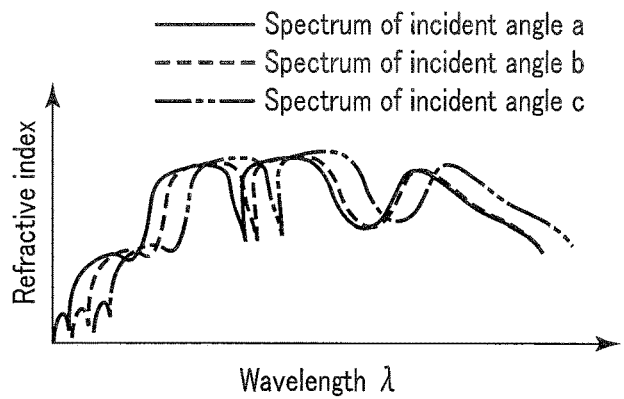
FIG. 15 is a graph showing another example of the sensing part of the curvature sensor shown in FIG. 2 and showing reflection spectra of the sensing part.

The sensing parts 36 can be formed by a plurality of dielectric films laminated in the thickness direction. For example, one (dielectric film) 36 of the sensing parts 36 has a reflection spectrum having reflectance as shown in FIG. 15. The dielectric film has characteristics that it absorbs light that has not been reflected. As shown in FIG. 15, the dielectric film has characteristics that the reflection spectrum varies such that the wavelength band shifts depending on the incident angle of light. If the sensing parts 36 are formed by laminating a plurality of dielectric films having different refractive indices and thicknesses appropriately, their reflection spectra (and absorption bands computed by subtracting the reflection spectrum from the spectrum of the light source) can freely be designed. It is thus possible to cause the reflection spectrum to vary among the sensing parts 36 when dielectric films are used for the sensing parts 36.

The sensing parts 36 can also be formed by combining resin materials containing a given amount of coloring matter as described above and a plurality of dielectric films as described above. In this case, a number of sensing parts 36 having a larger variety of absorption bands 46 and characteristic absorption bands can be achieved.

Figure 16:
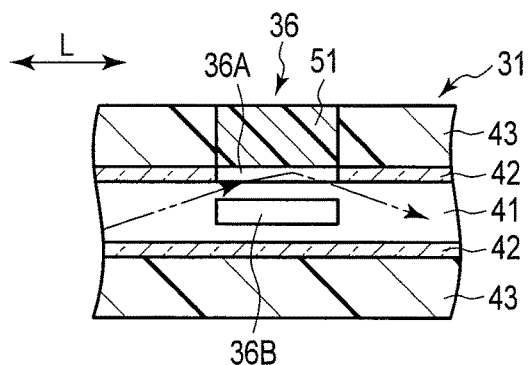
FIG. 16 is a sectional view showing another example of the curvature sensor shown in FIG. 2, crossing along the longitudinal direction of the light guide at a position of a sensing part.

As shown in FIG. 16, the curvature sensor 22 may have a dielectric film effect increasing resins 51 on (outside) sensing parts 36 (first portion 36A and second portion 36B). The dielectric film effect increasing resin 51 is provided very close to a dielectric film. The dielectric film effect increasing resin 51 is an example of members whose refractive index is higher than that of the core 41 of the light guide 31 and is made of resin whose refractive index is higher than that of the core 41. The dielectric film effect increasing resin 51 has the effect of easily leaking light to the sensing part 36 from the core 41. As the dielectric film effect increasing resin 51, a resin adhesive whose refractive index is, for example, 1.45 to 1.6 can be used.

A method of manufacturing the first portion 36A and the second portion 36B of the sensing part 36 will be described. The jacket 43 and the cladding 42 are partly subjected to, e.g. laser processing, photolithography, and etching in the longitudinal direction L to expose part of the core 41. If a micro-scratch is made on the core 41 at this time, light leaks to lose light to be guided and become vulnerable to bending; thus, it is favorable that they should be processed by a method to reduce scratches to a minimum.

According to the first embodiment, the curvature sensor 22 is provided along a flexible, linear detection target to allow a curvature of the detection target to be sensed, and the curvature sensor includes a light source; a light guide 31 provided along the detection target to guide light from the light source; a plurality of sensing parts 36 having light absorbability and provided along a longitudinal direction L of the light guide 31, the sensing parts 36 including absorption bands 46 having different intrinsic absorption patterns and characteristic absorption bands having intrinsic characteristic absorption patterns in the absorption bands 46; a light detector 33 which allows residual light not absorbed by the characteristic absorption bands to be detected, the residual light being included in light of bands corresponding to the characteristic absorption bands and radiated to the sensing parts 36 from the light source; and a calculator which computes a curvature of the detection target based on a rate of change in the residual light.

According to the foregoing structure, an absorption band and a characteristic absorption band can be set for each of the sensing parts 36 to make it possible to provide a plurality of sensing parts 36 along the longitudinal direction L of the light guide 31. Thus, a curvature of a detection target can be sensed with higher accuracy.

In this case, the band of the absorption band 46 of one 36 of the sensing parts 36 at least partly overlaps that of the absorption band 46 of another one 36 of the sensing parts 36. According to this structure, the absorption bands 46 are allowed to overlap each other to make it possible to provide a number of sensing parts 36 along the longitudinal direction L of the light guide 31.

The band of the characteristic absorption band of one 36 of the sensing parts 36 at least partly overlaps that of the characteristic absorption band of another one 36 of the sensing parts 36, and the absorptivity of the one characteristic absorption band 36 differs from that of the characteristic absorption band of said another sensing part 36.

According to this structure, even though the characteristic absorption bands are allowed to overlap each other, it is possible to find a point of the sensing part 36 at which the detection target is curved by the calculator by causing a difference in light absorptivity between the characteristic absorption bands. It is thus possible to further increase the number of sensing parts 36 arranged along the longitudinal direction L of the detection target and sense a curvature of the detection target with high accuracy.

The sensing parts 36 are made up of one of resin containing coloring matter, dielectric films, and a combination of the resin containing coloring matter and the dielectric films. This configuration makes it easy to design the absorption bands 46 and characteristic absorption bands intrinsic to the sensing parts 36 and makes it possible to compute a curvature by arranging a number of sensing parts 36.

The light guide 31 includes a core 41 and a cladding 42 which surrounds the core 41 and includes a plurality of storage sections arranged along the longitudinal direction L of the light guide 31 to store one or more sensing parts 36. The resin containing coloring matter has the same flexibility as that of the cladding 42. This structure makes it possible to provide a plurality of sensing parts 36 in the longitudinal direction L of the light guide 31 while the flexibility of the light guide 31 is maintained.

The light detector 33 includes a plurality of detection wavelength bands, and one of the detection wavelength bands has a portion that overlaps part of another one of the detection wavelength bands. According to this structure, a light detector 33 having a continuous detection wavelength band can be achieved, and a characteristic absorption band corresponding to the continuous detection wavelength band can be designed at a small pitch. It is thus easy to arrange a plurality of sensing parts 36 along the longitudinal direction L of a detection target and it is possible to improve the sensing accuracy of a curvature of the detection target.

The light source radiates light including part of the characteristic absorption bands. This structure makes it possible to improve the degree of freedom of the light source and achieve low costs by reducing constraints for material acquisition.

The light guide 31 includes a core 41 and a cladding 42 which surrounds the core 41 and includes a plurality of storage sections arranged along the longitudinal direction L of the light guide 31 to store a plurality of sensing parts 36. The sensing parts 36 are dielectric films, and a member whose refractive index is higher than that of the core 41 is brought into intimate contact with one surface of each of the dielectric films, which is opposed to the other surface contacting the core 41.

According to this structure, light can easily leak from the core 41 to the sensing parts 36 formed of dielectric films. Thus, light for sensing a curvature of a detection target can sufficiently be acquired and the sensing accuracy of the curvature can be improved.

[Second Embodiment]

An endoscope apparatus according to a second embodiment will be described with reference to FIGS. 27 and 28. An endoscope apparatus 11 of the second embodiment differs from that of the first embodiment in the structure of a second light source 32 of a curvature sensor 22, but the other elements are common to the first and second embodiments. Accordingly, a portion different from the first embodiment will mainly be described and the common elements will not be shown or described.

As shown in FIGS. 27 and 28, the second light source 32 is able to emit a plurality of light beams of different wavelength bands sequentially with time difference. FIGS. 27 and 28 show two light beams of different wavelength bands; however, the number of light beams of different wavelength bands is not limited to two. A plurality of wavelength bands capable of radiating from the second light source 32 correspond to the characteristic absorption bands of the sensing parts 36, respectively.

The second light source 32 includes a plurality of LEDs that are able to emit light beams of different wavelength bands and a control circuit section that causes the LEDs to emit light beams with time difference.

The light detector 33 has detection bands B corresponding to all of the characteristic absorption bands of the sensing parts 36, as in the first embodiment. Accordingly, the detection bands B of the light detector 33 correspond to all of the light beams of different wavelength bands, which are radiated from the second light source 32. The light detector 33 is formed of, e.g. silicon photodiodes.

According to the second embodiment, the curvature sensor 22 is provided along a flexible, linear detection target to allow a curvature of the detection target to be sensed, and the curvature sensor includes a light source being capable of radiating a plurality of types of light of different wavelengths with time difference; a light guide 31 provided along the detection target to guide light from the light source; a plurality of sensing parts 36 having light absorbability and provided along a longitudinal direction L of the light guide 31, the sensing parts including absorption bands 46 having different intrinsic absorption patterns and characteristic absorption bands having intrinsic characteristic absorption patterns in the absorption bands 46; a light detector 33 having a detection wavelength band which allows residual light not absorbed by the characteristic absorption bands to be detected, the detection wavelength band corresponding to all of the characteristic absorption bands of the sensing parts 36, the residual light being included in light of bands corresponding to the characteristic absorption bands and radiated to the sensing parts 36 from the light source; and a calculator which computes a curvature of the detection target based on a rate of change in the residual light.

According to the foregoing structure, as in the first embodiment, the rate of variations in light (residual light) reaching the light detector 33 can be detected by the bands corresponding to the characteristic absorption bands. In the second embodiment, furthermore, a plurality of types of light of different wavelengths are radiated from the light source with time difference; thus, the light detector 33 is able to receive information of light with time difference, and the residual light is separated satisfactorily. Thus, the detection resolution of the light detector 33 can be improved and the sensing accuracy of a curvature can be improved further. Furthermore, as the light detector 33, a simple one can be used, and the costs of the curvature sensor 22 can be lowered.

Various modifications can be made to the endoscope apparatus 11 and the curvature sensor 22 according to each of the foregoing embodiments without departing from the subject matter of the invention. Moreover, one invention can be made by combining the structural elements of the first embodiment and those of the second embodiment.

The curvature sensor 22 of the present invention can be applied to an illumination optical system provided at a hard end portion thereof, an image pickup device, an endoscope apparatus excluding an observation optical system including, e.g. a monitor and an objective, and a catheter. The curvature sensor 22 of the present invention can also be applied to an industrial endoscope apparatus as well as a medical endoscope apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A curvature sensor for sensing a curvature of a flexible, linear detection target, the curvature sensor comprising:
   a light source configured to generate light having a predetermined wavelength band;
   a light guide provided along the detection target, wherein the light guide is configured to guide the light generated by the light source;
   a plurality of sensing parts having light absorbability and provided along a longitudinal direction of the light guide, wherein the plurality of sensing parts have absorption spectral characteristics respectively, wherein the absorption spectral characteristics have different intrinsic absorption patterns at the wavelength band, and wherein characteristic absorption bands having intrinsic characteristic absorption patterns in the absorption spectral characteristics of each of the plurality of sensing parts are included in the wavelength band;

a light detector configured to:
receive light which is guided through the light guide from the light source and which passes through the plurality of sensing parts; and
detect the light in detection wavelength band including the characteristic absorption bands; and a calculator configured to compute a curvature of the detection target based on a rate of change in intensity of the light detected by the light detector,
wherein the number of the characteristic absorption bands included in the wavelength band is equal to or larger than the number of the plurality of sensing parts, and
wherein each of the plurality of sensing parts has different light absorptivity in each characteristic absorption band, the light absorptivity having a predetermined value other than zero.

2. The curvature sensor according to claim 1,
wherein the absorption spectral characteristic of one of the plurality of sensing parts has same part as the absorption spectral characteristic of another one of the plurality of sensing parts other than the characteristics absorption bands of the wavelength band.

3. The curvature sensor according to claim 1,
wherein the plurality of sensing parts comprises one of resin containing coloring matter, dielectric films, and a combination of the resin containing the coloring matter and the dielectric films.

4. The curvature sensor according to claim 1,
wherein the light guide comprises:
a core; and
a cladding surrounding the core and comprising a plurality of storage sections arranged along the longitudinal direction of the light guide to store the plurality of sensing parts,
wherein the plurality of sensing parts comprise resin containing coloring matter, and
wherein the resin has flexibility which is equal to flexibility of the cladding.

5. The curvature sensor according to claim 1,
wherein the light detector has the detection wavelength band including a plurality of detection wavelength regions, and one of the detection wavelength regions overlaps part of another one of the detection wavelength regions.

6. The curvature sensor according to claim 1,
wherein the light source is configured to radiate light including at least a part of wavelength components of the characteristic absorption bands.

7. The curvature sensor according to claim 1,
wherein the light guide comprises:
a core; and
a cladding surrounding the core and comprising a plurality of storage sections arranged along the longitudinal direction of the light guide to store the plurality of sensing parts,
wherein the plurality of sensing parts comprise dielectric films, and a member whose refractive index is higher than refractive index of the core is brought into intimate contact with one surface of each of the dielectric films which is opposed to the other surface contacting the core.

8. A curvature sensor for sensing a curvature of a flexible, linear detection target, the curvature sensor comprising:
a light source configured to radiate a plurality of types of light of different wavelength bands with time difference;
a light guide provided along the detection target, wherein the light guide is configured to guide the light radiated from the light source;
a plurality of sensing parts having light absorbability and provided along a longitudinal direction of the light guide, wherein the plurality of sensing parts have absorption spectral characteristics respectively, wherein the absorption spectral characteristics have different intrinsic absorption patterns at the wavelength bands, and characteristic absorption bands having intrinsic characteristic absorption patterns in the absorption spectral characteristics of each of the plurality of sensing parts are included in the wavelength band;
a light detector configured to:
receive light which is guided through the light guide from the light source and which passes through the plurality of sensing parts; and
detect the light in detection wavelength band including the characteristic absorption bands; and
a calculator configured to compute a curvature of the detection target based on a rate of change in intensity of the light which is detected by the light detector,
wherein the number of the characteristic absorption bands included in the wavelength band is equal to or larger than the number of the plurality of sensing parts, and
wherein each of the plurality of sensing parts has different light absorptivity in each characteristic absorption band, the light absorptivity having a predetermined value other than zero.

9. An endoscope apparatus comprising:
the curvature sensor according to claim 1; and
an insertion section, wherein the insertion section is the detection target whose curvature is to be sensed by the curvature sensor.

10. The curvature sensor according to claim 1,
wherein the light guide is configured to emit the light of the wavelength band having substantially uniform light intensity over all wavelength components included in the characteristic wavelength bands.

* * * * *